(12) United States Patent
Spasovski

(10) Patent No.: US 9,861,279 B2
(45) Date of Patent: Jan. 9, 2018

(54) METHOD AND DEVICE FOR DETERMINING THE EYE POSITION

(75) Inventor: Saso Spasovski, Berlin (DE)

(73) Assignee: CHRONOS VISION GMBH, Berlin (DE)

( * ) Notice: Subject to any disclaimer, the term of this patent is extended or adjusted under 35 U.S.C. 154(b) by 639 days.

(21) Appl. No.: 13/702,634

(22) PCT Filed: May 27, 2011

(86) PCT No.: PCT/DE2011/001123
§ 371 (c)(1),
(2), (4) Date: Jan. 9, 2013

(87) PCT Pub. No.: WO2011/157254
PCT Pub. Date: Dec. 22, 2011

(65) Prior Publication Data
US 2013/0120712 A1 May 16, 2013

(30) Foreign Application Priority Data
Jun. 19, 2010 (DE) .................. 10 2010 024 407

(51) Int. Cl.
A61B 3/113 (2006.01)
(52) U.S. Cl.
CPC .................... A61B 3/113 (2013.01)
(58) Field of Classification Search
CPC .......... A61B 3/113; A61B 3/103; A61B 3/14; A61B 3/1208; A61B 3/1225; G02B 27/0103; G02B 27/0172; G02B 27/0149; G01B 11/24; G01B 11/25

USPC ....... 351/205, 206, 209, 210, 220, 221, 246; 359/13, 630, 632; 382/103, 190, 191; 356/602, 603, 606
See application file for complete search history.

(56) References Cited

U.S. PATENT DOCUMENTS 5,471,542 A 11/1995 Ragland
6,019,755 A 2/2000 Steinert
(Continued)

FOREIGN PATENT DOCUMENTS

DE 19719695 A1 11/1998
DE 102006002001 A1 7/2007
(Continued)

OTHER PUBLICATIONS

English translation of DE19719695, machine translated on May 4, 2016.*
International Search Report dated Dec. 2, 2011.

Primary Examiner — Jie Lei
(74) Attorney, Agent, or Firm — Hauptman Ham, LLP

(57) ABSTRACT

The invention relates to a method and device for determining eye position, wherein a light pattern is produced on the surface of an eye by means of a light source and an image of the light pattern produced on the eye is recorded by means of an image recording apparatus, wherein points of the transition region between the sclera and the iris of the eye are determined from the image of the light pattern by means of an image processing apparatus. The coordinates of the calculated points are calculated by triangulation or stereo-vision, and the position of the iris plane or a plane oriented parallel thereto is determined from said coordinates. The limbus of the eye and the center thereof can also be determined in three dimensions.

20 Claims, 12 Drawing Sheets

(56) References Cited

U.S. PATENT DOCUMENTS

| | | | |
|---|---|---|---|
| 6,079,829 A * | 6/2000 | Bullwinkel | 351/210 |
| 6,179,422 B1 * | 1/2001 | Lai | 351/210 |
| 6,299,307 B1 * | 10/2001 | Oltean | A61B 3/113 |
| | | | 351/210 |
| 2001/0022648 A1 | 9/2001 | Lai | |
| 2005/0024586 A1 * | 2/2005 | Teiwes | A61B 3/113 |
| | | | 351/209 |
| 2006/0215111 A1 | 9/2006 | Mihashi | |
| 2008/0252849 A1 | 10/2008 | Van Saarloos | |

FOREIGN PATENT DOCUMENTS

| | | |
|---|---|---|
| WO | 9918868 A1 | 4/1999 |
| WO | 0027273 A1 | 5/2000 |
| WO | 0134021 A1 | 5/2001 |
| WO | 01/89373 A2 | 11/2001 |

\* cited by examiner

19a

METHOD AND DEVICE FOR DETERMINING THE EYE POSITION

RELATED APPLICATIONS

The present application is National Phase of International Application Number PCT/DE2011/001123, filed May 27, 2011, and claims priority from German Application Number 10 2010 024 407.4, filed Jun. 19, 2010.

The invention relates to a method and a device for determining the eye position and/or the viewing direction.

BACKGROUND OF THE INVENTION

It is important to determine the eye position and viewing direction for very different applications, for example in the field of medical engineering. In the case of laser-based eye surgery or laser ablation, in which corneal tissue of the eye is ablated by means of laser pulses, the precise eye position must be known. However, establishing the eye position is also essential in the field of balance research, as it is in the further development of human/machine interfaces, for example in the field of vehicle control. In the field of advertisement and visual communication, knowledge of the viewing direction of the observer is an important factor for assessing the quality of graphics, for example in view of incentives for purchasing, which are offered on websites, billboards and videos.

In order to measure and track the eye position, use is made of so-called "eye trackers". In the case of a laser treatment, this is used to determine the correct alignment of a laser beam in order to ensure the precise position of the tissue ablation. This is necessary because rapid eye movement may occur during a treatment and this can lead to a positioning error of the laser pulses relative to the eye. The so-called pupil tracking supplies the lateral position of the pupil (x-direction, y-direction), while a cyclotorsion tracker determines the rotation of the eye about the viewing direction (z-direction).

Document DE 102004020356 A1 describes a method for capturing eye movements, in which image sequences of an eye are captured using an optoelectronic sensor. Here, an area of the head is provided with markers, which are likewise captured. The movement of the eye in the head is established from the obtained image data, taking into account the pupil center and the markers on the head.

Patent DE19954047B4 shows a method for measuring eye movements, in which non-toxic tincture markers are applied with a predetermined geometry onto the conjunctiva of the eye and image sequences of the eye are captured using an optoelectronic sensor. From this, coordinates of a rotationally neutral reference point are established which coordinates are related to the coordinates of the markers in order to calculate the eye position therefrom.

Document DE102008049846A1 shows a further method for measuring the eye movement. Here, the sclera of the eye is illuminated by coherent light such that a spot pattern is created by interfering light which was scattered on the sclera. A displacement of the recorded spot pattern is established on the basis of two cropped images, and the eye movement is determined therefrom.

Document DE102008039838A1 describes a method for applications in medical engineering for scanning the three-dimensional surface of an object by means of a light-beam scanner, in which the triangulation principle is applied. If a pattern is projected onto the object surface, the distance information in respect of all points of the pattern in a camera image can be calculated.

U.S. Pat. No. 4,761,071 shows a device and a method for determining the topography of the cornea and the sclera of the eye by means of triangulation. Here, a fluorescence substance is introduced into the eye and illuminated by an incident light beam. The fluorescence radiation is captured from another direction and the elevation of the eye surface is determined by triangulation.

In most known eye tracking systems, the eye position is captured by means of recorded camera images in a plane which is usually situated in the eye plane which is parallel to the transversal/vertical body plane (x-y plane). However, in order to determine the eye position completely, establishing the tilt of the eyeball is of importance in addition to knowledge of the lateral position of the pupil (x-y position) and the rotation of the eye about the viewing direction (z-direction). If the tilt is disregarded, there is a decentration error DE on the eye surface.

The decentration error is shown in FIG. 2. Here, a pupil 2 of an eye and the cornea 4, situated thereover at a distance APC, is schematically illustrated in two positions, namely initially in a first state 2a without tilt and furthermore in a second state 2b, in which it is tilted toward the right in the image. The angle α describes the angle of the tilt with respect to the normal state in which the eye is not tilted. The pupil is situated at a distance PCR from the center of rotation 1 of the eye. In the non-tilted, first state 2a, a central point 4a of the cornea 4 is situated precisely above the center of the pupil 2. If an image of the eye is captured from the viewing direction, the point 4a on the cornea 4 is situated at the same point in the image as the pupil center. If the eye is tilted about the center of rotation 1, this results in a lateral displacement LS of the center of the pupil 2 in the captured image of the eye. However, the central point 4a of the cornea 4 in the captured image of the eye no longer lies at the same point as the pupil center but rather is situated at a distance therefrom, which forms the decentration error DE.

By way of example, if in the case of laser ablation the point 4a is tracked as a predetermined ablation center in accordance with the lateral displacement LS, this results in a current ablation center 3 on the cornea 4 which is displaced by the decentration error DE with respect to the predetermined ablation center 4a. This results in an ablation which deviates from the intended position despite tracking. If the decentration error DE is to be taken into account, the tilt of the eye needs to be known.

The knowledge of the tilt angle is a necessary but not sufficient condition for correcting the error DE. Thus, for an exact correction, further parameters need to be known: the distance APC between pupil 2 and cornea 4 and the distance PCR between the center of rotation 1 and the pupil 2. If statistical means are used for these parameters, the error DE is at least reduced. However, the missing parameters are usually known from preliminary examinations.

In the case of laser ablation, the importance of correcting the treatment decentration, which is created by the tilt of the eye, increases with increasing shot frequency. If a frequency of approximately 100 Hz is assumed, a typical treatment has a duration of about 100 s. If the tilt of the eye is normally distributed in terms of direction and magnitude at this time, this then leads to the treatment "smearing." Although the amount of volume ablated is approximately as intended, the treatment diameter increases and so the achieved ablation depth decreases as a function of the standard deviation of the tilt movement. If the tilt during the treatment is not distributed normally or, in an extreme case, systematically tilted, the ablation for various directions will deviate to a different extent from the intended ablation even in the case of low shot frequencies, and induced refractive errors may occur. If the frequency is e.g. 1000 Hz, the duration of a typical treatment reduces to 10 s. The probability of the tilt of the eye being distributed normally during this short period of time reduces and short deviations from the viewing direction can have drastic effects.

In order to establish the tilt of the eye, document DE102004025999A1 shows a device which comprises a reference object which is positioned on the eye. A sensor apparatus captures the reference object in two translational directions, and three further sensors capture the respective distance from three scanning points on the reference object. A computer unit establishes the position of the reference object in real time. However, a disadvantage of this device is that the reference object in the form of a ring needs to be placed onto the eye such that it is concentric with the pupil.

SUMMARY OF THE INVENTION

It is the object of the invention to specify a method by means of which the eye position and/or the viewing direction can be measured as precisely and as quickly as possible, while taking into account the tilt of the eye. Furthermore, a device is to be developed, by means of which the eye position or the viewing direction and the tilt of the eye can be determined precisely and quickly.

This object is achieved by the method for determining the eye position and/or the viewing direction as per patent claim 1, and by the device as per patent claim 12. Further advantageous features emerge from the dependent claims, the description and the drawings.

The basic idea of the invention consists of the fact that a light pattern is created on the eye surface in order to determine the eye position and an image of the light pattern imaged on the eye surface is captured, wherein points of the transition region between sclera and iris are established from the image of the captured light pattern, the coordinates of which points are calculated and these coordinates are used to determine the position of the iris plane or a plane aligned parallel thereto. As a result, it is possible to determine the eye position, the viewing direction and, in particular, the tilt of the eye as well in a very quick fashion and with great accuracy, wherein it is not necessary to place objects onto the eye in advance.

Furthermore, the method according to the invention further provides the option of establishing the lateral pupil positions. The light pattern vanishes in the pupil, i.e. it is interrupted abruptly. The edge of the pupil can be established from the abrupt interruption of the pattern.

By way of example, the light pattern is projected onto the eye. It can also be created on the eye surface by the use of a grating or reflection grating or by diffractive elements.

The coordinates of the points (P1, P2, P3, P4) are preferably calculated by triangulation. An advantage of this method lies in a particularly high speed. However, it is also possible to determine the coordinates by means of stereovision. To this end, use is made of one or more additional cameras. The use of one camera and a plurality of mirrors and/or prisms is also feasible. Or use is made of only one camera and only one additional mirror: the (single) camera observes the scene directly with e.g. the left sensor half and observes the mirror with the other half, said mirror showing the scene from a different angle. It is also possible likewise to use stereovision with the aid of at least two image carriers, which image the scene on the camera chip from different viewing angles, and one camera.

A further advantageous option for determining the coordinates of the points lies in the so-called "depth from focus" method. Here, the focal objective-lens plane is moved through the measurement volume in a targeted fashion. At any one time, only those parts of the light pattern situated in the current focal plane are rich in contrast.

The points in the image are advantageously established such that they are situated on the sclera in the direct vicinity of the iris. This results in an even higher accuracy because the light is not refracted at interfaces within the eye. At least three points are necessary, without there being an upper limit. The accuracy of the result increases with the number of points that are determined.

The points are preferably established from discontinuities in the imaged light pattern at the boundary between sclera and iris. As a result, it is possible to establish precisely those points at which the light pattern intersects the transition region between sclera and iris.

If the discontinuity is too small, for example for anatomical reasons, it is also possible to search for a brightness gradient along the lines because the lines are, in general, brighter on the sclera. It is also possible for an image processing method to be used to search for the limbus in the camera image. The points are then established from the intersection of the lines with the limbus.

The light pattern created on the eye is advantageously formed from individual lines or line fragments, the virtual intersection of which with the limbus of the eye is calculated by an approximating function in order to identify the points. An advantage of this is that no part of the light pattern is projected onto the iris, and so no light enters the eye during the measurement.

The light pattern is preferably projected or imaged onto the eye at an angle of incidence. An obliquely incident imaging beam or projection beam for projecting the light pattern onto the eye results in a very high accuracy when applying the triangulation or light-intersection method for determining the position of the points at which the light pattern is reflected.

In particular, the light pattern can be formed from light stripes or light rings, wherein the light stripes can be aligned e.g. parallel to one another and the light rings can be aligned e.g. concentrically to one another. However, the light pattern can also be formed from light stripes in the form of a cross. The result of this is great flexibility depending on the respective purpose of the measurement and, depending on the application case, an optimization of the measurement accuracy.

The light pattern can advantageously also comprise one or more broad stripes, which for example have a sharp edge and need not necessarily have a rectangular and parallel embodiment.

The light pattern is preferably multicolored and is, for example, captured by a color camera. This increases the information content of the images: the image processing unit can, for example, find the stripes on the basis of the color and distinguish these from one another. This can avoid ambiguity in identifying the stripes if use is made of many stripes or other complicated patterns. A further advantage consists of the fact that the white sclera and colored iris have different absorption properties. The colored stripes scattered or reflected by the sclera have a different color composition after being recorded by means of a camera than those coming from the iris. This can be used when searching for the limbus. Here noticeable gradients in the color profile are to be expected along the lines.

The degree and the direction of a tilt of the eye are preferably established from the normal vector of a plane spanned by the points.

By way of example, calibration is effected by virtue of projecting the light pattern onto a planar surface, which is displaced in the direction of the optical axis of a camera or image capture apparatus during the calibration process. The planar surface is displaced in the direction of the z-axis. As a result, it is possible to relate very precisely displacements of the light pattern in the recorded image to the elevation position and elevation structure of the surface on which the light pattern is imaged during the measurement. The displacement is not necessarily in the direction of the camera.

During the measurement it is possible for the light pattern to be moved over the eye or for time-varying light patterns to be created. By way of example, in the process, the lines of the light pattern can be moved such that they are always positioned in optimum fashion with respect to the edge of the limbus. If the light pattern is moved, it is also possible to use e.g. only one line as pattern. Then, the line has moved sufficiently far between two camera recordings and the movement of the eye can simultaneously be disregarded in the case of an appropriately high speed.

Since both eyes look in the same direction if one fixates on a relatively distant point, the light pattern can also, for example, be projected onto the one eye in order to establish the viewing direction or eye position of the other eye. This is advantageous because an eye treated by refractive surgery has a very rough surface and can thereby influence the results.

It is advantageous for both eyes to be in the field of view of the camera, even if only one eye is measured. As a result, it is possible to ensure that the correct eye is treated. The ratio of the sides of the camera sensor advantageously is 3:1. As a result, it is possible to record both eyes without loss of resolution.

It is possible to establish a twist of the head or the head torsion from the angle between the line connecting both pupil centers and a constant reference line.

The device according to the invention for capturing the eye position comprises an apparatus for creating a light pattern on a surface of the eye, and an image capture apparatus for capturing the light pattern created on the surface of the eye, wherein provision is made for an image processing unit, which establishes a plurality of points from the captured light pattern at which the sclera of the eye adjoins the iris, wherein the image processing unit calculates the spatial coordinates of the points established thus and, from this, establishes the position of the iris plane or a plane aligned parallel thereto.

By way of example, the image processing unit can be part of the camera. Specific camera types do not require an external processing unit. In this case, the image-processing algorithms run internally in a processor and/or directly on the sensor.

In particular, the image processing unit can be designed such that it establishes the points such that these lie on the sclera in the direct vicinity of the iris.

The image processing unit is advantageously designed such that it identifies the points from discontinuities in the projected light pattern at the boundary between sclera and iris. However, the points can also be established from brightness or color gradients along the lines.

In particular, the apparatus for creating the light pattern can be controlled such that a plurality of individual lines or line fragments are projected onto the eye as light pattern, wherein the image processing unit for example calculates the virtual intersection of the line fragments with the limbus of the eye by an approximating function in order to identify the points.

In particular, it is possible for a glass fiber image bundle to be arranged in the beam path in front of the image capture apparatus in order to capture the projected light pattern on the eye. As a result, it is possible to reduce either the exposure time of the camera or the intensity of the pattern generator. The glass fiber bundle is coherent and can, as a result, be used for image transmission.

The device can be provided with a control apparatus for controlling a laser ablation unit which, if the eye position changes, tracks the ablation beam thereof or deflects said ablation beam from the eye or interrupts said ablation beam. As a result, ablation errors as a result of a change in the eye position are avoided.

Provision is advantageously made for a fluorescence-light sensor for capturing ablation points on the eye which were hit by the ablation beam, wherein the computer unit for example establishes the spatial coordinates of the captured ablation points by e.g. triangulation. As a result it is possible, for example in the case of laser ablation, to register each individual ablation spot on the basis of the emitted fluorescence light and the focus of the projection thereof on the sensor surface can be determined at a high frequency.

In particular, it is possible to establish all three spatial coordinates of the hit surface by means of triangulation. A relief map of the external corneal surface emerges from the sums thereof.

In particular, the device according to the invention is designed such that it is suitable for carrying out the method according to the invention and has appropriate features.

DESCRIPTION OF PREFERRED EXEMPLARY EMBODIMENTS

In the following text, the invention will be described closer and in more detail on the basis of preferred exemplary embodiments, with reference being made to the drawings. Features which are described in the context of the method also apply to the device, and vice versa. Here:

Figure 4A:
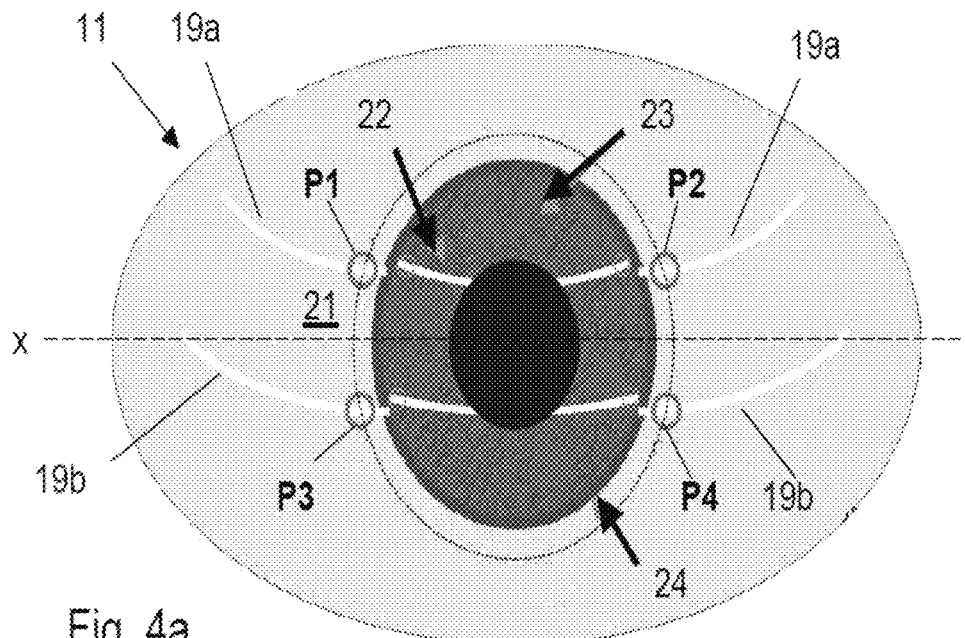
Figure 4B:
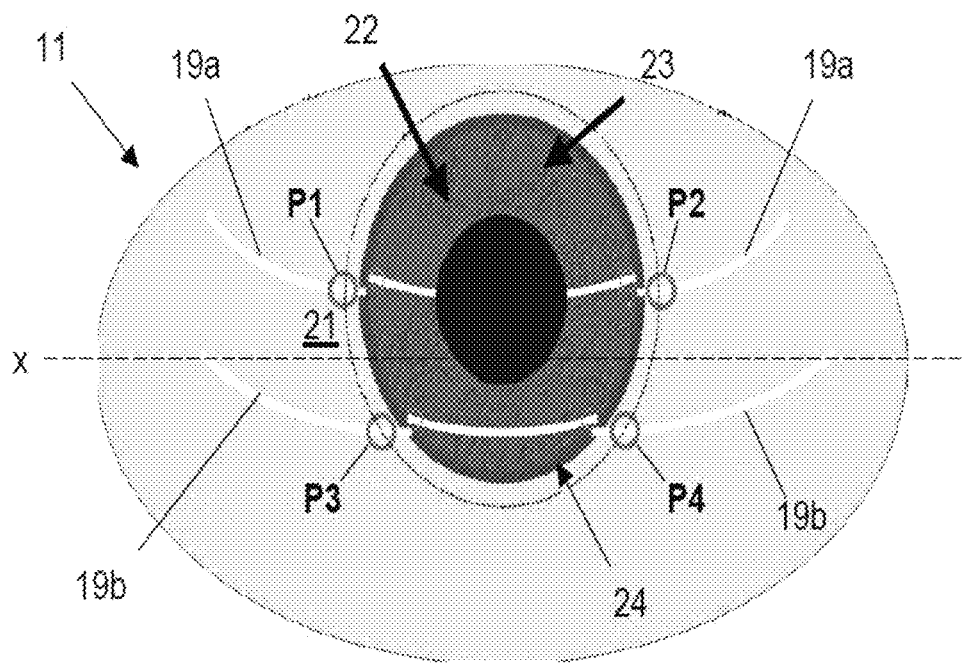
Figure 5A:
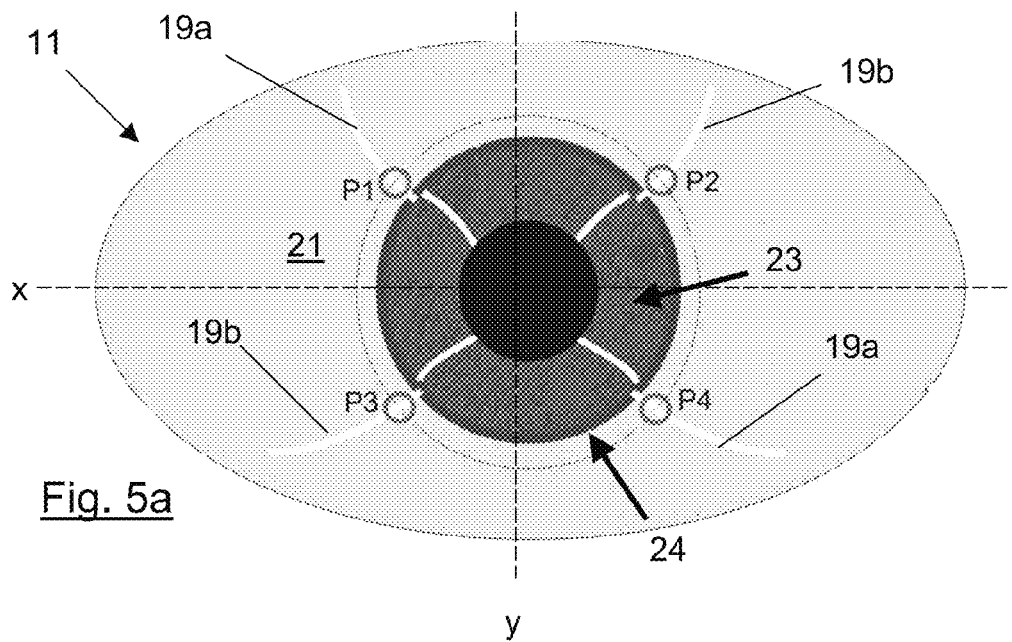
Figure 5B:
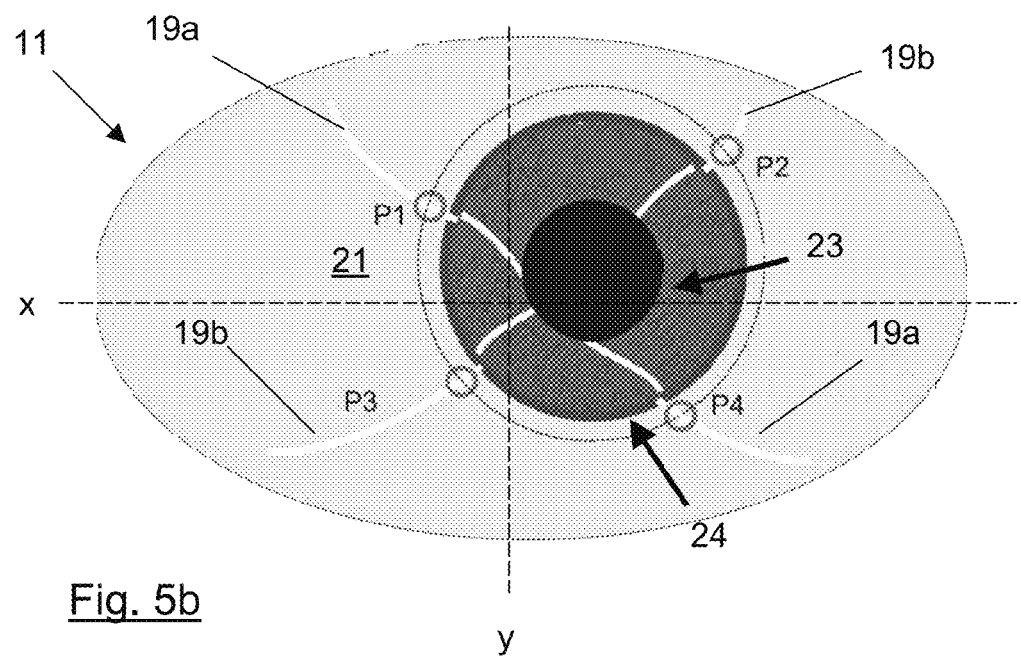
Figure 5C:
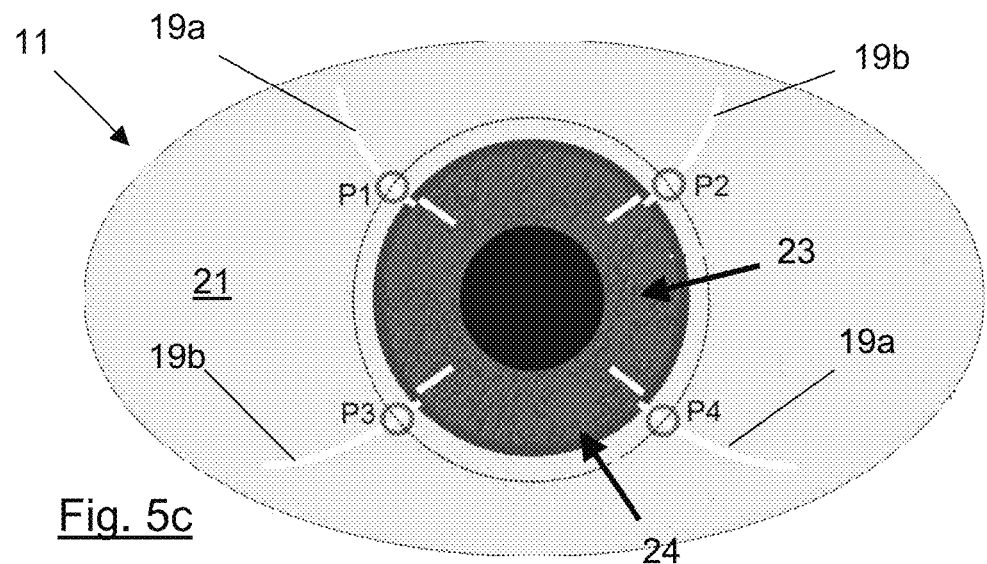
Figure 6:
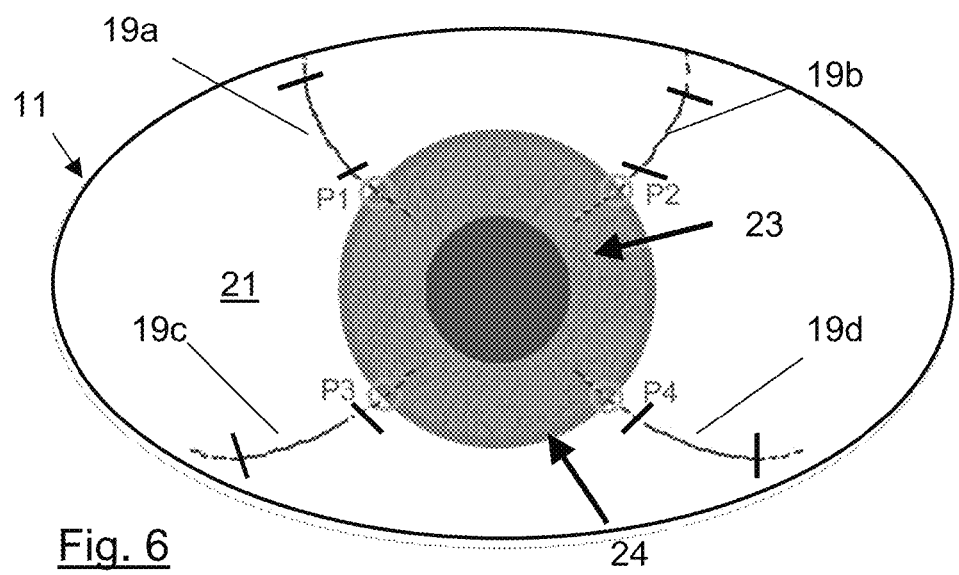
Figure 7:
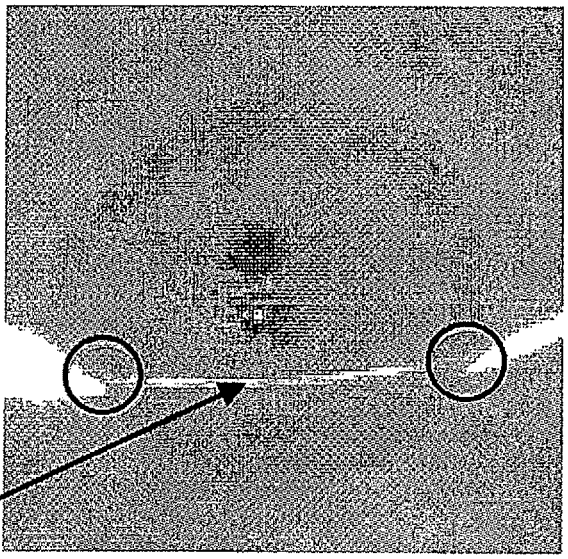
Figure 8:
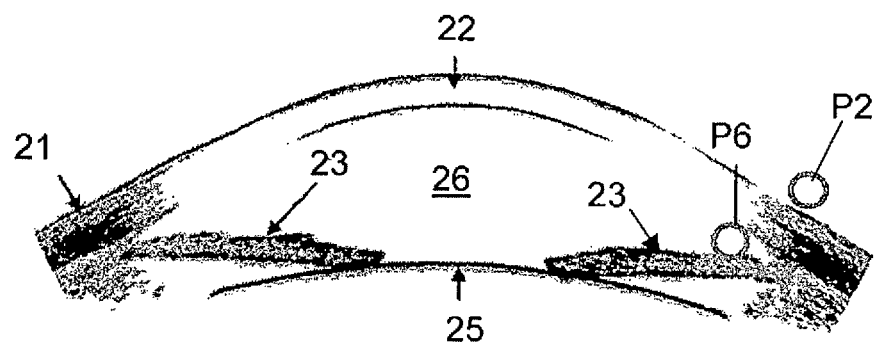
Figure 9:
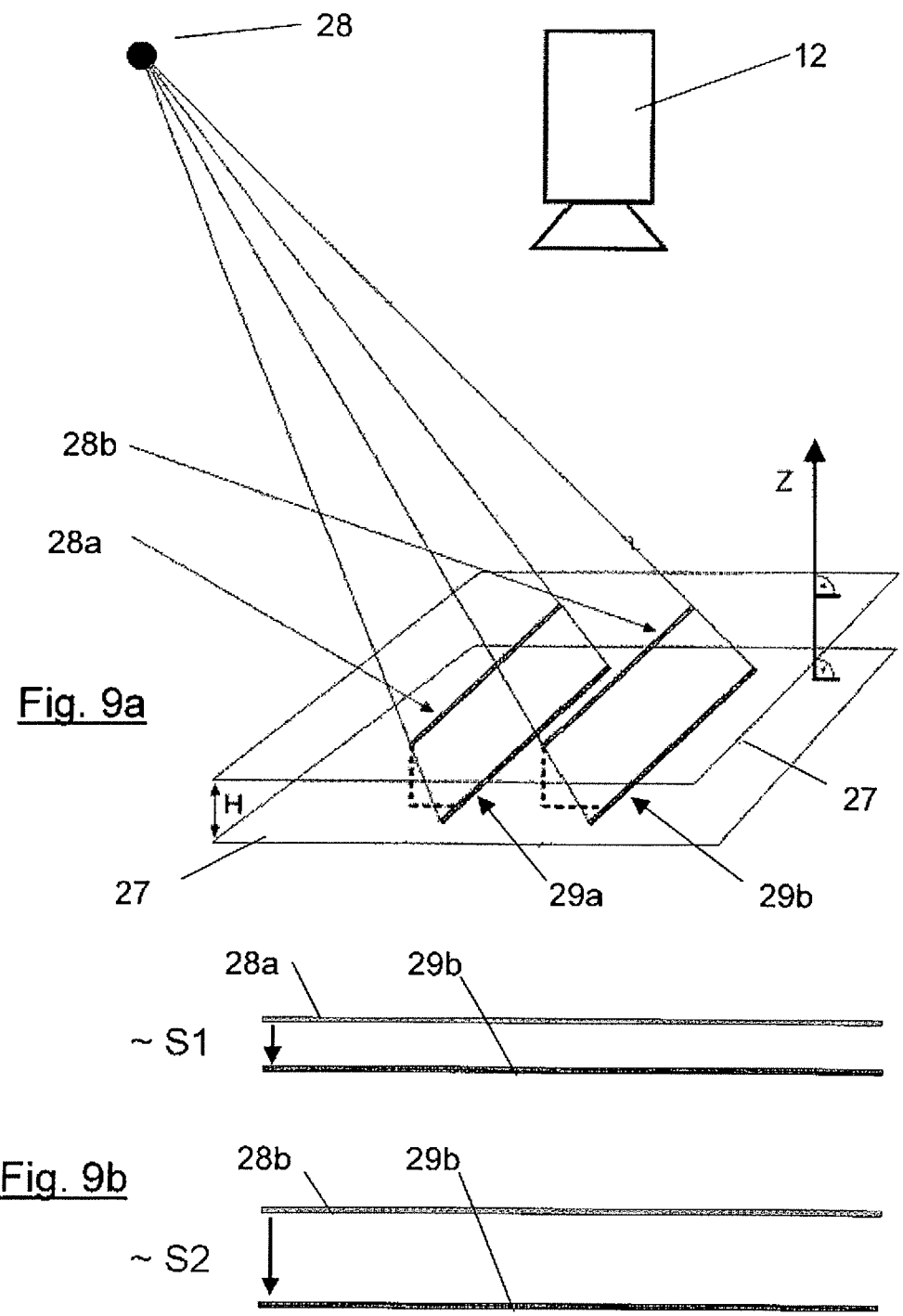
Figure 10:
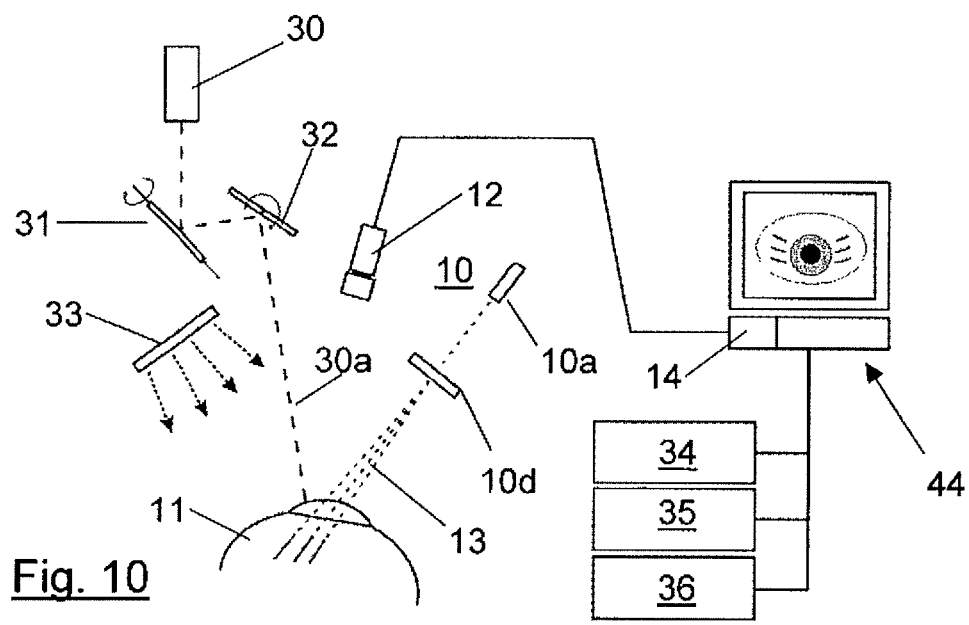
Figure 11:
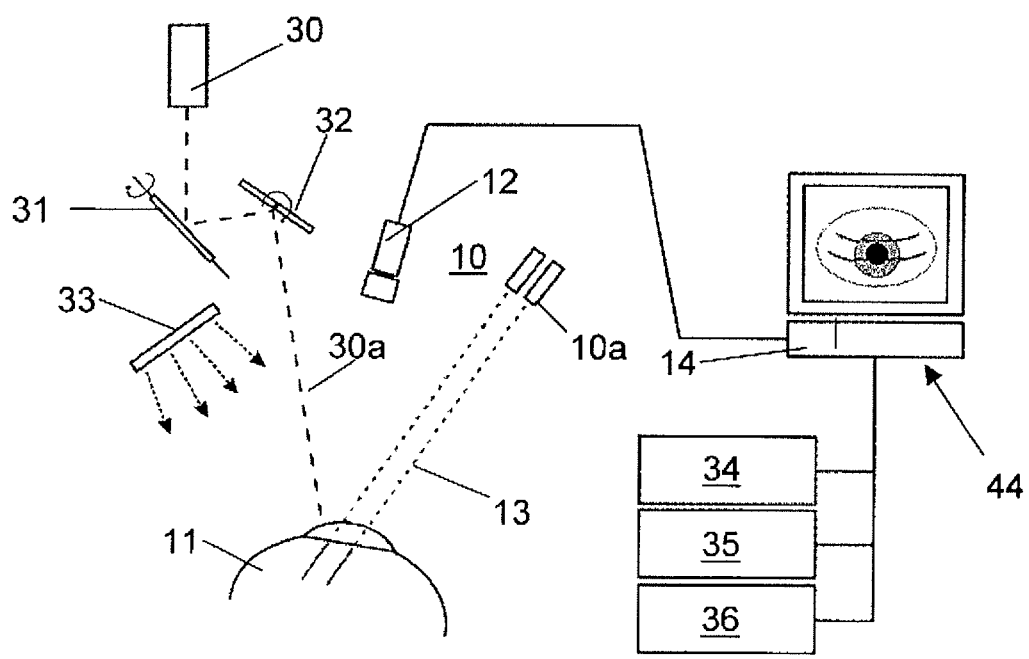
Figure 12:
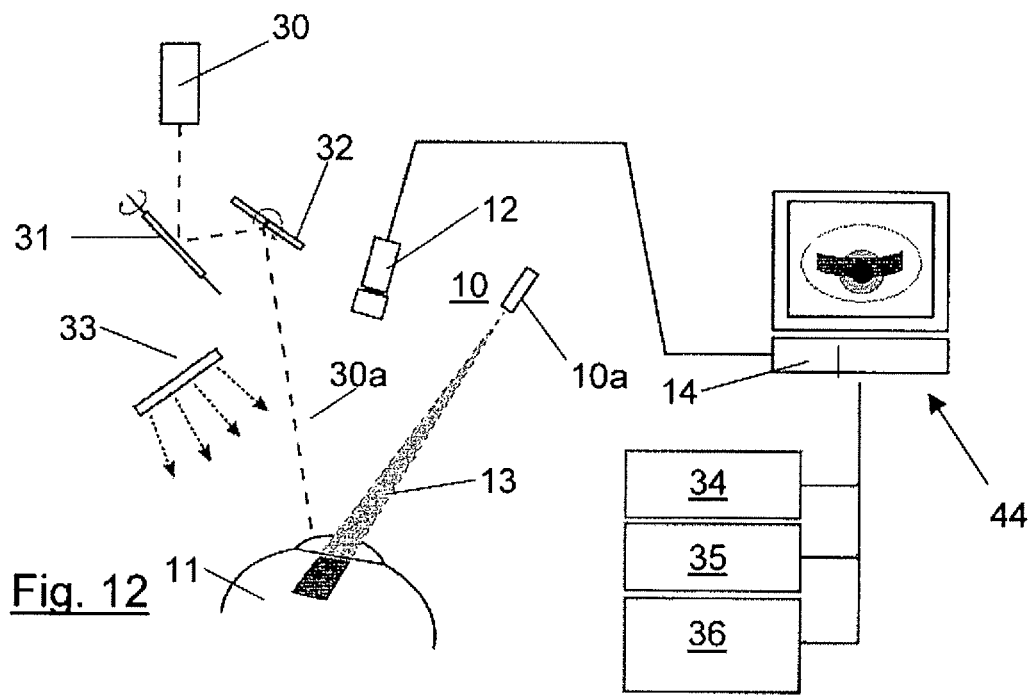
Figure 13:
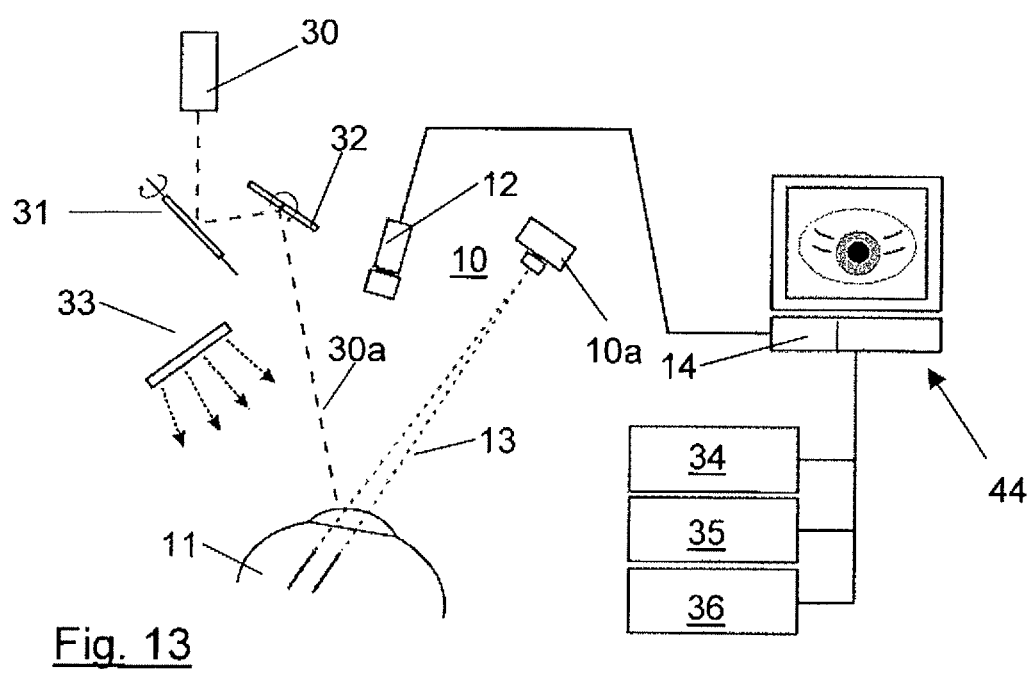
Figure 14:
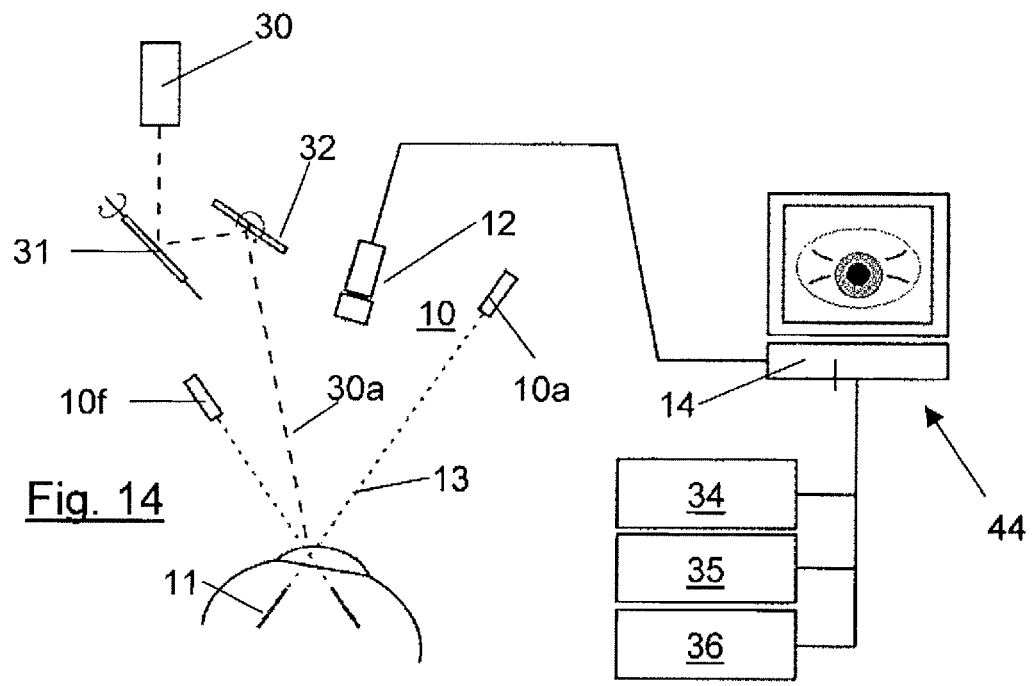
Figure 15:
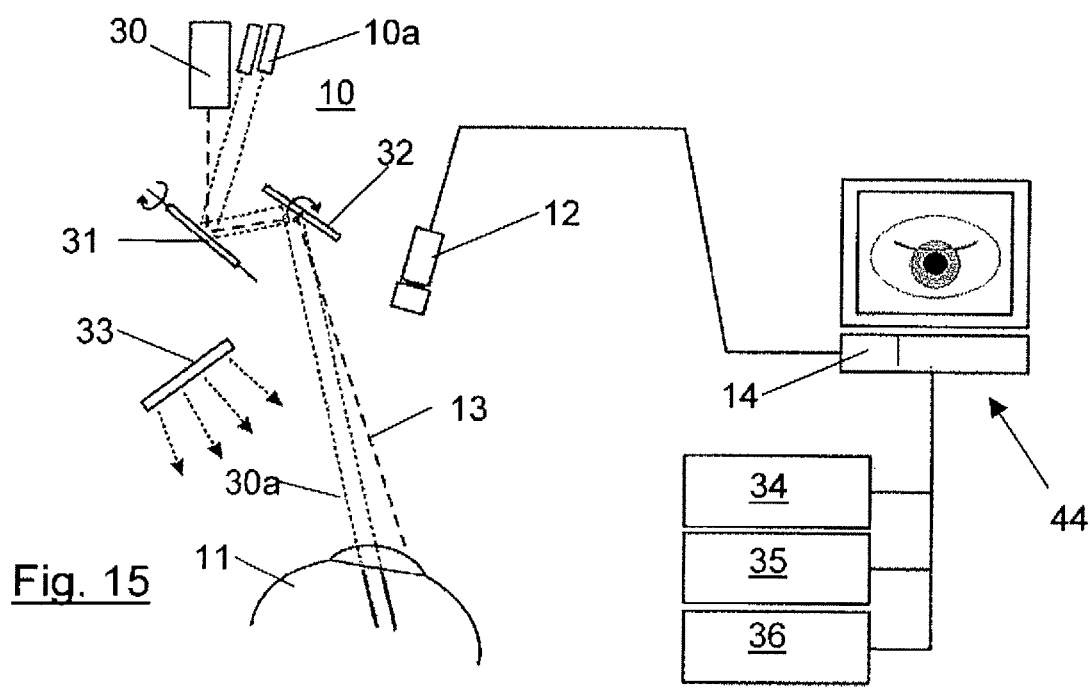
Figure 16:
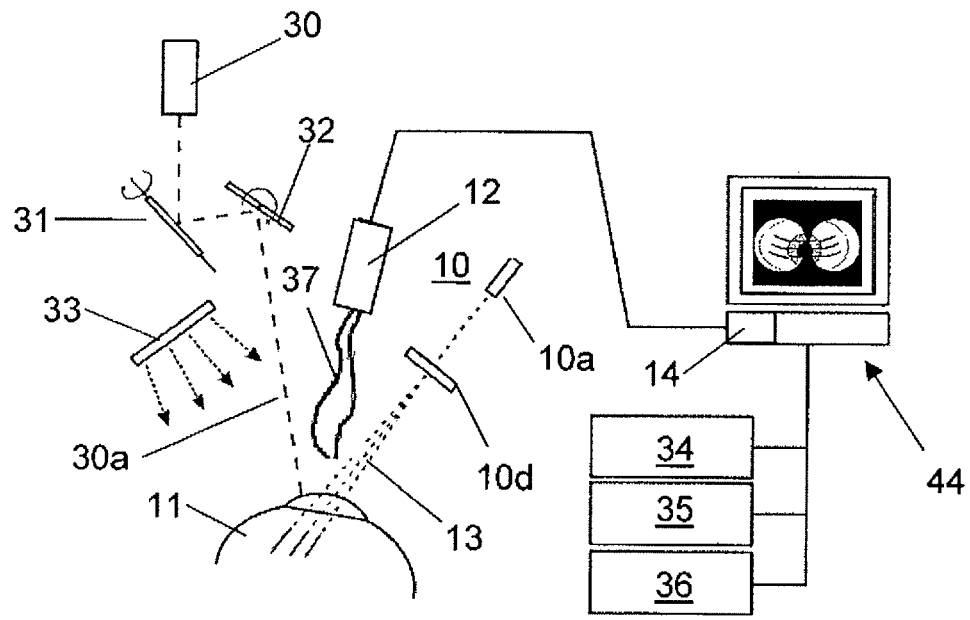
Figure 17:
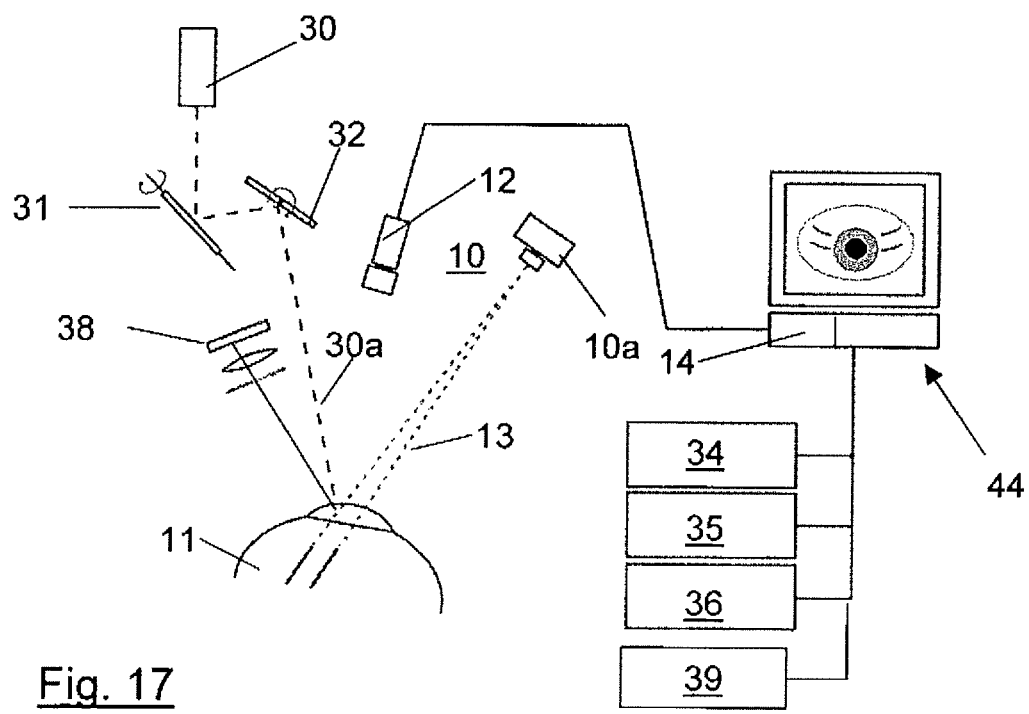
Figure 18:
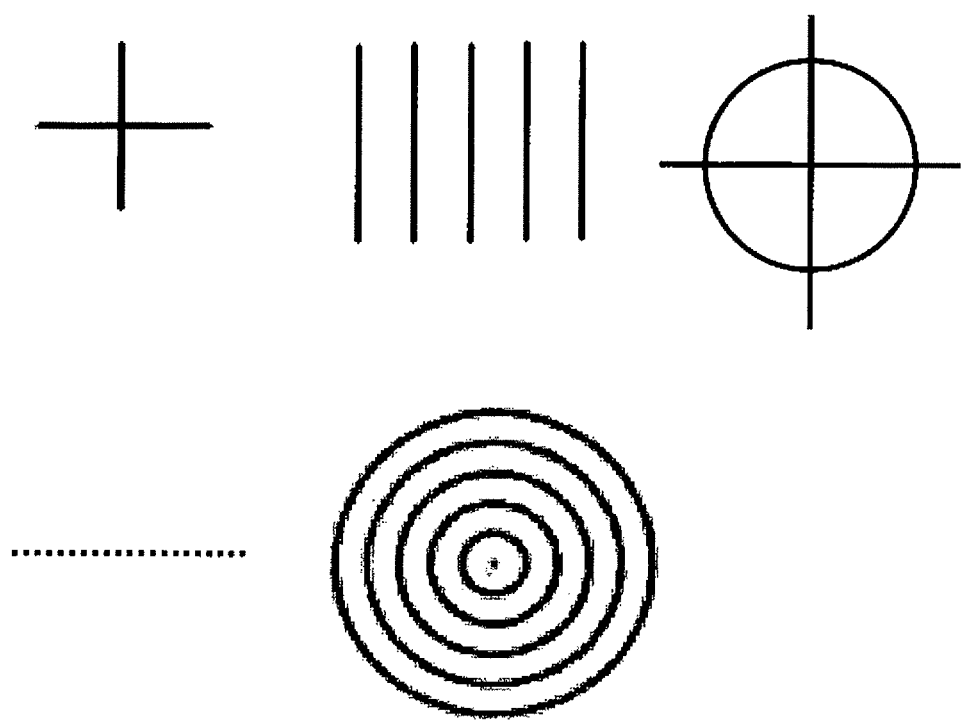

FIGS. 4a and 4b schematically show the image of an eye on which, according to the invention, parallel light stripes are imaged;

FIGS. 5a to 5c schematically show the image of an eye with a static cross projected thereon according to the invention;

FIG. 6 schematically shows the image of an eye onto which, according to the invention, lines have only been projected in the region of the sclera;

FIG. 7 shows a real image of an eye on which, according to the invention, a light line has been imaged;

FIG. 8 shows a schematic sectional view of an eye in the region of the iris;

FIGS. 9a and 9b show a principle design for calibrating the device according to the invention and a calibration example;

FIG. 10 shows a second preferred embodiment of the device according to the invention with a laser and a diffractive optical element;

FIG. 11 shows a third preferred embodiment of device according to the invention with a number of lasers as projection apparatus;

FIG. 12 shows a fourth preferred embodiment of the device according to the invention, by means of which a broad light stripe is created;

FIG. 13 shows a fifth embodiment of the device according to the invention with a beamer as projection unit;

FIG. 14 shows a sixth preferred embodiment of the device according to the invention, by means of which the light pattern is projected onto the eye from various directions;

FIG. 15 shows a seventh preferred embodiment of the device according to the invention, by means of which a pattern is moved over the eye;

FIG. 16 shows an eighth preferred embodiment of the device according to the invention with a glass fiber bundle in front of the camera;

FIG. 17 shows a ninth preferred embodiment of the device according to the invention with a fluorescence-light sensor; and FIG. 18 shows various light patterns, for imaging according to the invention on the eye.

Figure 1:
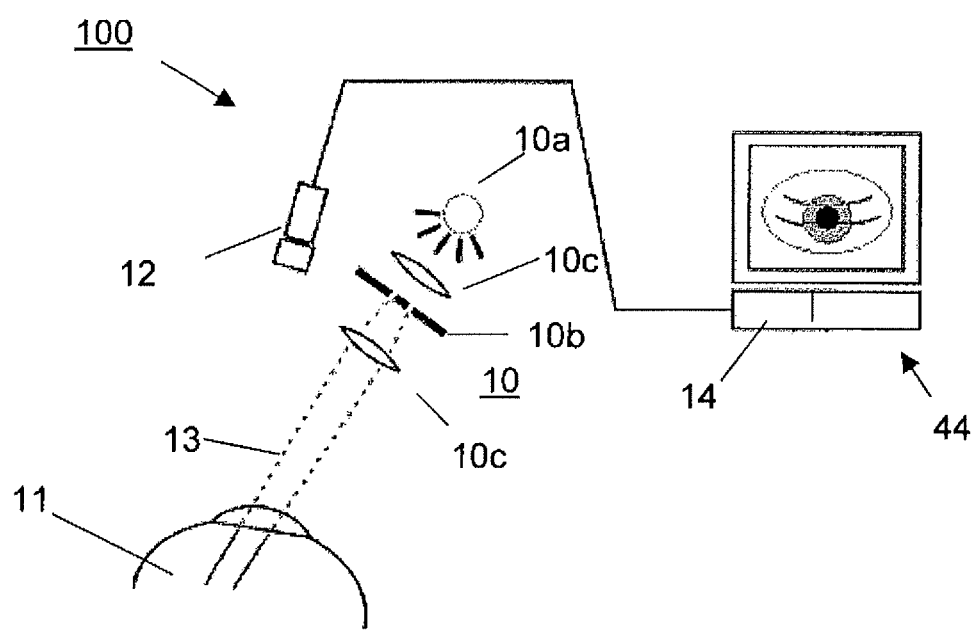
FIG. 1 shows a schematic illustration of a first preferred embodiment of the device according to the invention.

FIG. 1 illustrates a device 100 for determining the eye position as preferred embodiment of the invention. A projection apparatus 10, consisting of a light source 10a, a slit element 10b for creating a double slit, and a lens system 10c, serves for creating a light pattern and projecting the latter onto an eye 11 by means of light beams 13. An image capture apparatus in the form of a camera 12 captures the light pattern imaged on the eye 11. Here, the optical axis of the camera 12 is at an angle to the beam path of light beam 13 of the projection onto the eye 11 for the purpose of recording the image on the eye 11. The camera 12 is coupled electrically to an image processing unit 14 which, in the present case, is part of a computer unit 44. However, the image processing apparatus can also be realized elsewhere, for example in the camera itself.

As a result of the angle between the projected light beam 13 and the recording direction of the camera 12, it is possible to determine an elevation profile of the light pattern imaged on the eye 11 by application of the triangulation method or light-section method.

Figure 3:
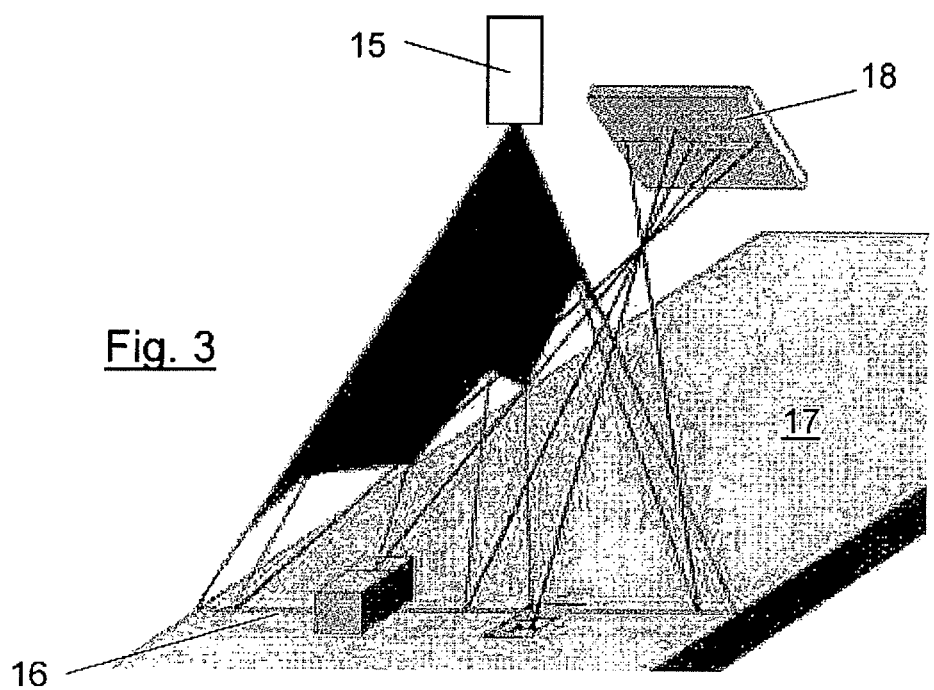
FIG. 3 shows a schematic illustration of the triangulation method.

FIG. 3 shows the principle of the light-section method or triangulation method. A laser 15 is used to project a light stripe 16 as a pattern onto the surface of an object 17. An image sensor 18 captures the light stripe 16 imaged on the surface from a direction that differs from the direction of the light beam of the laser 15 incident on the object surface 17. As a result of the angle between the incident light beam and the light beam scattered or reflected toward the image sensor 18, it is possible to determine the elevation of the object surface 17 in the region of the light stripe or else the respective distance from the image sensor 18 from the position of the light stripe 16 in the recorded image.

FIGS. 4a and 4b show the eye 11 with two static lines 19a, 19b imaged thereon, said lines forming a light pattern. Here, the lines 19a, 19b are aligned parallel to one another during the projection or imaging, but the image thereof on the eye 11 is, as a result of the curvature of the sclera 21 and refraction by the cornea 22, likewise curved. As seen from the observer or the camera, the iris 23, which is substantially planar, and the limbus 24 are situated behind the cornea 22. While the eye 11 in FIG. 4a is not tilted, the eye 11 shown in FIG. 4b is tilted upward. Here, the tilted eye 11 exhibits a position with an upward viewing direction, corresponding to a tilt of the eye about the x-axis. At the same time, it is possible to identify a lateral upward displacement, i.e. in the y-direction, of the iris 23 compared to the untilted position illustrated in FIG. 4a.

At the transition between the sclera 21 and the cornea 22, the lines 19a, 19b are respectively interrupted as a result of the elevation difference at the edge of the limbus and form a discontinuity at this point.

The image processing apparatus 14 (see FIG. 1) is designed such that it establishes the points at which the lines 19a, 19b created on the eye 11 have discontinuities or brightness or color gradients. By way of example, this occurs by virtue of the fact that the brightest regions are identified as lines and dark areas situated therein are identified as interruptions. The position of the interruptions or discontinuities of the lines 19a, 19b is used to establish, by means of image processing, points P1, P2, P3, P4 which are situated on the lines 19a, 19b and are arranged outside of the iris 23, but are in the direct vicinity of or adjoin the latter.

The points P1, P2, P3, P4 can be used to calculate a planar circle in $R^3$ space. The normal of the circle plane constitutes the normal vector of the limbus or iris. Moreover, it is possible to determine the tilt angle α via the scalar product with the z-axis. The axis of rotation is perpendicular to the plane spanned by the z-axis and the normal vector of the limbus. The limbus center emerges in three dimensions from the center of the planar circle and it can be used instead of the pupil during e.g. eye tracking.

FIGS. 5a, 5b and 5c schematically show a plan view of the eye 11, with the lines 19a, 19b being formed as a static cross during the projection thereof. The lines 19a, 19b appear curved on the eye, as explained above. While FIG. 5a illustrates the eye 11 in an uptilted position, the eye 11 is tilted top right in FIG. 5b. That is to say there is a tilt about both the x-axis and the y-axis. At the same time, limbus 24 and iris 23 are laterally displaced toward the top right in the image, or rather in the x- and y-direction. In the image illustrated in FIG. 5c, the central part of the cross is not present. Projecting a pattern without the central part is advantageous in that possible algorithms that include the iris 23 are influenced less. The points of the discontinuities of the lines 19a, 19b are established by the image processing apparatus 14, and the points P1, P2, P3 and P4 are determined therefrom.

FIG. 6 shows an image of the eye 11 in which the lines 19a, 19b, 19c, 19d are kept so short that they are only imaged on the sclera 21, but not in the region of the iris 23. In the figure, the start and end points of the lines 19a, 19b, 19c, 19d are marked by short delimiting stripes. In order to determine the points P1, P2, P3, P4, the lines 19a, 19b, 19c, 19d are lengthened by the image processing apparatus 14 (see FIG. 1) by means of an approximating function in order to form a virtual intersection with the limbus 24. An advantage of this is that no light pattern is imaged on the iris 23. It is self-evident that this is also possible with other patterns, for example during the illumination with parallel lines.

FIG. 7 shows a real recording of the human eye, with a line 19a projected onto the eye, wherein the discontinuities of the line 19a at the transition between sclera 21 and iris 23 are readily identifiable.

FIG. 8 shows a section through the eye in the region of the iris 23, with the cornea 22 situated thereover and with the lens 25. At the outer edge of the cornea 22, the sclera 21 is situated outside of the region of the iris 23. Aqueous humor is situated in the chamber 26 between the iris 23 and the cornea 22. The discontinuities of the projected lines 19a, 19b, 19c, 19d (see FIGS. 4 to 6) are due to the elevation difference between iris and limbus. In the figure, a discontinuity is marked by the points P2 and P6, which represent the end points of an imaged line at the interruption thereof.

When carrying out the method for determining the eye position, the camera 12 shown in FIG. 1 observes the scene and an algorithm realized in the image processing apparatus 14 identifies the lines which are imaged on the eye 11 by the projection apparatus 10. As a result of triangulation and a preceding calibration of the system it is possible to establish the 3D coordinates x, y, z for each line pixel. In order to determine the tilt of the limbus plane those parts of the lines are identified which are situated in the direct vicinity of the iris 23 but outside thereof. These parts of the lines are marked as points P1, P2, P3, P4 in FIGS. 4 to 6.

For visualization purposes, the point P2 is illustrated as an example in FIG. 8. As a result of the anatomy of the eye, the points P1, P2, P3, P4 in FIGS. 4 to 6 virtually lie in a plane which is aligned parallel to the iris plane. This procedure takes into account the fact that the lines projected onto the eye 11 are refracted from their original direction by the cornea and the aqueous humor situated in the chamber 26 before they reach the iris 23. The light of the portions of the lines 19a, 19b that are projected onto the iris 23 in turn, on their path from the iris 23 to the camera 12, pass through the aqueous humor situated in the chamber 26 and, subsequently, the cornea 22, and so there is once again refraction at the involved interfaces, i.e. at the interface between aqueous humor and inner corneal surface and at the interface between outer corneal surface and air.

If the pixels of the lines situated on the iris 23 were used for triangulation calculations, e.g. the point P6 in FIG. 8, the results would be falsified and the establishment of the tilt of the eye would be erroneous. Substantially two factors would be responsible for this error:

a) as a result of the described refraction, the line 19a, 19b impinges on the iris 23 at an angle that differs from the angle of incidence. This leads to an error in the elevation coordinate or the distance coordinate in the z-direction.
b) secondly, the refraction also leads to the lateral coordinates x and y being falsified.

By contrast, the line sections are not refracted on the sclera 21 and therefore, in the method according to the invention, provide the basis for determining the tilt of the eye and the limbus center in three dimensions.

The above-described discontinuities in the projected or imaged lines 19a-d are distinctive features, which are used in determining the limbus. A plane whose normal vector specifies the viewing direction is calculated or approximated with the aid of points P1, P2, P3, P4. The degree of the tilt of the eye 11 is calculated from the angle which the normal vector includes with the z-axis. The tilt direction emerges from the difference vector of viewing direction and z-axis. The cross product of viewing direction and z-axis defines the axis of rotation of the tilt. That is to say the absolute alignment of the eye 11 or the viewing direction is calculated, and not the alignment relative to an initial time. As a result of calculating the plane by means of a few points, the algorithm in the image processing apparatus 14 is very fast.

FIGS. 9a and 9b schematically show a possible calibration of the device according to the invention for determining the eye position. For the purposes of the calibration, use is made of a planar surface 27 which varies in terms of its elevation during the calibration. During the calibration process, a line generator 28 creates two light lines 28a, 28b on the surface 27. In the process, the light from the line generator 28 impinges obliquely or at an angle of incidence on the surface 27 for projecting the light lines 28a, 28b. The lines 28a, 28b are recorded by the camera 12. In a next step, the surface 27 is displaced vertically or in the z-direction by the value H, i.e. away from the camera 12 in the illustrated example. However, the axis of the camera need not necessarily correspond to the displacement direction of the calibration plane. In this second position of the surface 27, the light lines 29a, 29b imaged thereon are displaced with respect to their respective preceding position 28a or 28b. Here, the displacement S1, S2 (see FIG. 9b) of the line position is a measure for the lift H of the calibration plane. However, it is self-evident that the calibration can be applied not only to line patterns, but rather to all other types of projected light patterns as well.

FIG. 10 shows a further embodiment of the invention, in which the projection apparatus 10 has a laser 10a or an LED unit as a light source. The features described in the context of FIG. 1 also apply to FIG. 10 and the following, further embodiments. Situated in the beam path of the projection or light beam 13 there is a diffractive optical element 10d for creating the light pattern on the eye 11. By way of example, the diffractive optical element creates a number of parallel lines as light pattern, which are projected onto the eye 11.

An optional illumination unit 33, which is preferably an infrared-light source, for example in the form of an LED arrangement, serves to illuminate the scene. However, if the projected light pattern is bright enough to be detected, and the projected pattern or the line intersects with the limbus, it is also possible to detect the edge of the limbus without additional illumination as a result of the occurring discontinuity in the light pattern. However, if the position of the limbus in the image must be known, sufficient illumination is to be ensured such that the latter can be determined by means from image processing. However, the ambient light also often suffices for the image recording in the case of sensitive cameras.

In the example illustrated here, the device for determining the eye position is coupled to a laser ablation apparatus, in which an ablation laser 30 guides an ablation laser beam 30a onto the cornea of the eye 11 by means of horizontally and vertically pivotable scanning mirrors 31, 32. A computer unit 44 is connected electrically to a control apparatus 34 for controlling the ablation laser 30, and to a control apparatus 35 for controlling the scanning mirrors 31, 32 and to a control unit 36 for controlling the light source 10a which serves to create the light pattern for determining the eye position.

The control apparatus 34 actuates the ablation laser 30 such that the ablation laser beam 30a is interrupted once a specific tilt of the eye 11 has been met such that there is no further tissue ablation.

The control apparatus 35 actuates the scanning mirrors 31, 32 such that the ablation laser beam 30a is tracked in accordance with the tilt of the eye. However, optionally said laser beam can also be guided to an absorber such that, for example in the case of too great a positional deviation from the intended value, there is no ablation.

The control apparatus 36 actuates the light source 10a such that the light beam for creating the light pattern is suppressed in the case of too great a deviation of the eye position or the viewing direction. As a result, no radiation enters the eye through the pupil.

It is furthermore possible by means of the control apparatus 36 to create the light pattern in pulsed operation. An advantage of this lies in a lower radiation exposure if the pattern creation is synchronized to the image creation.

However, the light pattern projected onto the eye 11 can for example also be created in every second camera image. In this case, it is also possible to detect low intensity patterns by forming the difference between successive images.

By coupling the device according to the invention to an apparatus for laser ablation it is possible to correct a treatment in real time. The shots or laser pulses are tracked in accordance with the respective tilt a of the eye. Hence, the fact that the angle of incidence deviates from the intended value in the case of any tilt of the eye is taken into account. In the case of large tilt values, the mirrors 31, 32 can be actuated such that the laser beam is deflected from the eye or interrupted in order to discontinue the treatment.

Figure 2:
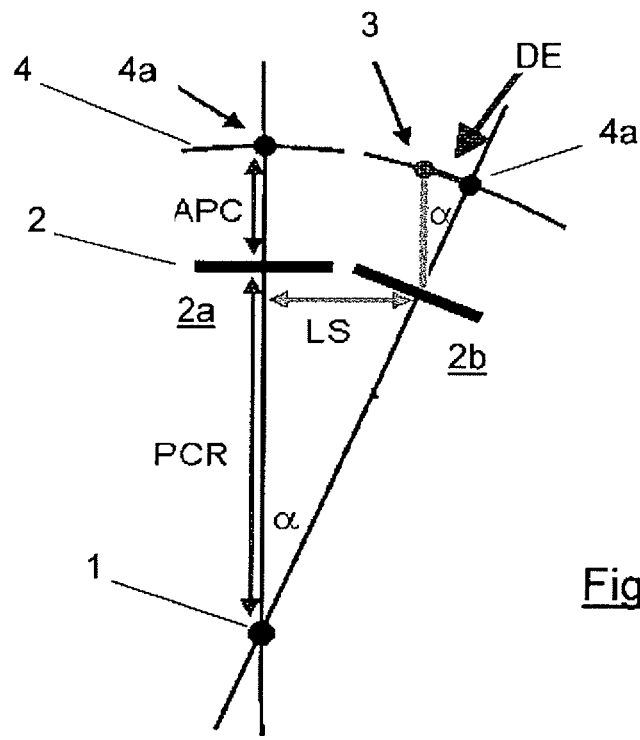
FIG. 2 shows a tilt of the eye and the decentration error resulting therefrom if the eye tilt is not taken into account.

The magnitude of the central decentration DE emerges from the trigonometric relationships as illustrated in FIG. 2. The decentration DE is determined by the tilt angle and the anterior chamber depth APC. Here the following applies:

$$DE/APC = \tan(\alpha).$$

In the case of a tilt angle of 7 degrees and an anterior chamber depth APC of 4 mm, the magnitude of the central decentration DE emerges to be 0.5 mm. Taking into account the refractive effect of the cornea, this results in a value of approximately 0.4 mm for DE.

As a result of a filter (not illustrated in the figure), which is optionally mounted in front of the camera 12, the fluorescence radiation ($\lambda$<400 nm) emitted by the tissue hit under laser fire or else the ambient light ($\lambda$<800 nm) is blocked. Here, the filter transmits wavelengths used during the creation of the light pattern. As a result, the calculation in respect of the tilt of the eye and the limbus center is uninfluenced by the ablation procedure and can occur during the latter.

All light sources are suited to be a light source 10a for creating the light pattern provided that the spectral sensitivity of the selected camera 12 or image capture apparatus is sufficiently high at the emitted wavelengths.

In order to suppress extraneous light, a scene is often illuminated by IR light in refractive surgery and an IR filter is placed. In these cases, it is advantageous likewise to provide an IR source as light source 10a for the pattern creation. However, it is also advantageous outside of refractive surgery to use a light source whose light is invisible to humans and therefore does not glare.

However, this glare can also be avoided by virtue of a pattern being created which does not enter the pupil and which is switched off in the case of extreme movements. It is predominantly areal sensors which for example have digital or analog embodiments that are suitable as light sensors in the image capture apparatus or camera 12.

The following text shows even more embodiments with alternative light sources 10a. In respect of the description of the remaining elements, reference is made to the preceding figures and the associated description of the figures.

FIG. 11 shows an advantageous embodiment of the device according to the invention, in which a number of n lasers or LEDs with an integrated line optical unit are used as a light source 10a.

In the alternative shown in FIG. 12, the light source 10a consists of a beamer or projector or an LED or laser with a diffractive optical element. A broad, sharply delimited light stripe is created.

In the example shown in FIG. 13, a beamer or projector is used as light source 10a. This is advantageous, particularly for creating time-changeable light patterns such as e.g. lines that are moved such that they are always positioned optimally with respect to the edge of the limbus.

FIG. 14 shows a further alternative, in which, in addition to the light source 10a which is embodied in the form of an LED or a laser with integrated line optical unit, a further light source 10f is present, which projects a line pattern or any other pattern onto the eye 11 from another direction.

Finally, FIG. 15 shows a further exemplary embodiment, in which the light source 10a for creating the pattern on the eye 11 is arranged such that the light pattern is guided onto the eye 11 via the scanning mirrors 31, 32. Here the control unit 36 actuates the scanning mirrors 31, 32 accordingly. The scanning mirrors 31, 32 can be the same as the ones by means of which the ablation laser beam 30a is guided onto the cornea of the eye 11. That is to say the light pattern for determining the eye position is in this case moved with the aid of the deflection or scanning mirrors 31, 32 of the ablation laser 30. If the movement of the pattern occurs sufficiently quickly, a single line only is, in principle, also possible as a pattern. Then the line has moved sufficiently far between two camera recordings and, at the same time, the movement of the eye can be disregarded. Care has to be taken that, e.g. in the case of two parallel lines, use is only made of those recordings in which the two lines "intersect" the limbus. This need not always be the case, particularly if the mirrors guide the treatment beam onto the edge region of the treatment zone.

By way of example, it would also be possible for a mirror flipping between two states to cast a line onto the eye. Two successive images then see two differently positioned lines. The movement should be synchronized with the camera 12. As a result, the algorithm is simplified because only one line has to be emitted per image.

FIG. 16 shows two glass fiber bundles 37 arranged in front of the camera 12 which are embodied as image carriers by means of which the projected pattern is recorded. As a result, it is possible to reduce either the exposure time of the camera 12 or the intensity of the pattern generator or the light source 12.

In FIG. 17, a fluorescence-light sensor 38 or PSD sensor with an appropriate filter has been additionally arranged and it detects every ablation spot on the basis of the emitted fluorescence light and which can establish the focus of its projection on the sensor surface with a frequency of a number of kHz. The PSD sensor is controlled by the control apparatus 39. A computer unit establishes the 3D coordinates of the hit point by means of triangulation. This is how, in combination with the established eye position, a real-time ablation monitor is developed.

FIG. 18 shows possible geometries for the light pattern for imaging on the eye in order, as described above, to establish the tilt of the eye about the x-axis and/or y-axis and to determine the eye position or the location of the eye or else the viewing direction.

In particular, the present invention can also be used to establish the limbus of the eye and the center thereof in three dimensions in space. This can be brought about in conjunction with determining the alignment of the limbus/iris plane.

LIST OF REFERENCE SIGNS

1 Center of rotation of the eye
2 Pupil
2a, 2b First and second state of the pupil
3 Current ablation center
4 Cornea
4a Central point of the cornea
10 Projection apparatus
10a Light source 10b Double slit
10c Lens system
10d Diffractive optical element
11 Eye
12 Camera
13 Light beam
14 Image processing apparatus
15 Laser
16 Light stripe
17 Object
18 Image sensor
19a, 19b Lines
19c, 19d Lines
21 Sclera
22 Cornea
23 Iris
24 Limbus
25 Lens
26 Chamber
27 Planar surface
28 Line generator
28a, 28b Light lines (first position)
29a, 29b Light lines (second position)
30 Ablation laser
30a Ablation laser beam
31, 32 Mirrors
33 Illumination unit
34 Control apparatus for an ablation laser
35 Control apparatus for mirrors
36 Control apparatus for a light source
37 Glass fiber bundles
38 Fluorescence-light sensor
39 Control apparatus for a fluorescence-light sensor
44 Computer unit
100 Device

The invention claimed is:

1. A method for determining the eye position, in which points of a transition region between sclera and iris of the eye are established, the coordinates of which points are calculated and this is used to determine the position of the iris plane or a plane aligned parallel thereto, wherein
   a light pattern is projected onto a surface of the eye such that it intersects the transition region between sclera and iris,
   an image of the light pattern projected onto the eye surface is captured, from which the points of the transition region between sclera and iris are established, and
   the method further comprises calculating spatial coordinates x, y and z of the points by triangulation, wherein an elevation of the surface on which the light pattern is projected is determined via the use of a displacement of the light pattern.

2. The method as claimed in claim 1, wherein the points are established from discontinuities in the captured light pattern at the boundary between sclera and iris or from a brightness gradient and/or color gradient of the light pattern.

3. The method as claimed in claim 1, wherein the light pattern projected onto the eye is formed from line fragments.

4. The method as claimed in claim 1, wherein the light pattern is formed from light stripes or light rings, which are aligned parallel and concentrically, respectively, to one another.

5. The method as claimed in claim 1, wherein the light pattern is formed from light stripes in the shape of a cross.

6. The method as claimed in claim 1, wherein the degree and the direction of a tilt of the eye are established from the normal vector of the plane spanned by the points.

7. The method as claimed in claim 1, characterized by a calibration, in which the light pattern is projected onto a planar surface, which is displaced relative to the image capture apparatus during the calibration.

8. The method as claimed in claim 1, wherein the light pattern is moved over the eye or that time-varying light patterns are created.

9. The method as claimed in claim 1, wherein the light pattern which is created on one eye of a pair of eyes is used to establish the viewing direction or eye position of the other eye.

10. The method as claimed in claim 1, wherein both eyes are in the field of view of a camera.

11. The method as claimed in claim 1, wherein a twist of a head or a head torsion is established from the angle between a line connecting both pupil centers and a constant reference line.

12. The method as claimed in claim 1, wherein the captured image of the light pattern projected onto the eye's surface includes least one of discontinuities, different brightness or color gradients.

13. The method as claimed in claim 1, wherein the light pattern forms a pattern on the surface of the eye.

14. The method as claimed in claim 1, wherein the light pattern is projected from a first location, and the image is captured at a second location spaced away from the first location such that there is a first angle between the light pattern traveling from the first location to the eye and light traveling from the eye to the second location, and wherein the points are calculated owing to the presence of the first angle.

15. The method as claimed in claim 1, further comprising calculating spatial coordinates x, y and z of the points by triangulation, and determining spatial coordinates of the surface on which the light pattern is projected via the use of a position of the image of the light pattern.

16. A method for determining the eye position, in which points of a transition region between sclera and iris of the eye are established, the coordinates of which points are calculated and this is used to determine the position of the iris plane or a plane aligned parallel thereto, wherein
   a light pattern is projected onto a surface of the eye such that it intersects the transition region between sclera and iris,
   an image of the light pattern projected onto the eye surface is captured, from which the points of the transition region between sclera and iris are established,
   the light pattern projected includes discontinuities, and wherein the method further comprises using the discontinuities of the light pattern projected onto the eye to establish the points at which the sclera of the eye adjoins the iris, and
   the method further comprises calculating spatial coordinates x, y and z of the points by triangulation, wherein an elevation of the surface on which the light pattern is projected is determined via the use of a displacement of the light pattern.

17. The method as claimed in claim 16, further comprising calculating spatial coordinates x, y and z of the points by triangulation, and determining spatial coordinates of the surface on which the light pattern is projected via the use of a position of the image of the light pattern.

18. The method as claimed in claim 17, wherein the discontinuities are interruptions of lines or stripes, and wherein the position of the image of the light pattern corresponds to the position of the lines or stripes in the image of the light pattern.

19. The method as claimed in claim 16, wherein the discontinuities are interruptions of lines or stripes.

20. The method as claimed in claim 16, wherein the discontinuities are interruptions of lines or stripes, and wherein the position of the image of the light pattern corresponds to the position of the lines or stripes in the image of the light pattern.

\* \* \* \* \*